United States Patent [19]

Tomes

[11] Patent Number: 5,240,855
[45] Date of Patent: Aug. 31, 1993

[54] PARTICLE GUN

[75] Inventor: Dwight Tomes, Cumming, Iowa

[73] Assignee: Pioneer Hi-Bred International, Inc., Des Moines, Iowa

[21] Appl. No.: 906,374

[22] Filed: Jun. 30, 1992

Related U.S. Application Data

[63] Continuation of Ser. No. 351,075, May 12, 1989, abandoned.

[51] Int. Cl.5 ............................................. C12M 1/00
[52] U.S. Cl. .................................... 435/287; 935/85; 89/1.14; 435/284
[58] Field of Search ................. 435/172.1, 172.3, 287, 435/284; 935/52, 53, 85; 73/11, 12, 167; 604/68–70, 140, 141, 143; 89/1.14

[56] References Cited

U.S. PATENT DOCUMENTS 3,130,575  4/1964  Rogers ................................. 73/12
3,404,599  10/1968  Annis ................................... 73/12

OTHER PUBLICATIONS

Sanford et al. "Delivery of Substances into Cells and Tissues" Particulate Science and Tech. vol. 5 (1987) pp. 27–37.
Sanford, "The Biolistic Process", TIB Tech. vol. 6 (1988) pp. 299–302.

Primary Examiner—Michael G. Wityshyn
Assistant Examiner—William H. Beisner
Attorney, Agent, or Firm—Zarley, McKee, Thomte, Voorhees & Sease

[57] ABSTRACT

An improved particle gun for transporting biological substances such as nucleic acid into the cytoplasm of living cells. The gun has a barrel which is rifled to allow effective sealing on an acetal plastic macroprojectile within the barrel such that there is no blow-by of debris.

7 Claims, 2 Drawing Sheets

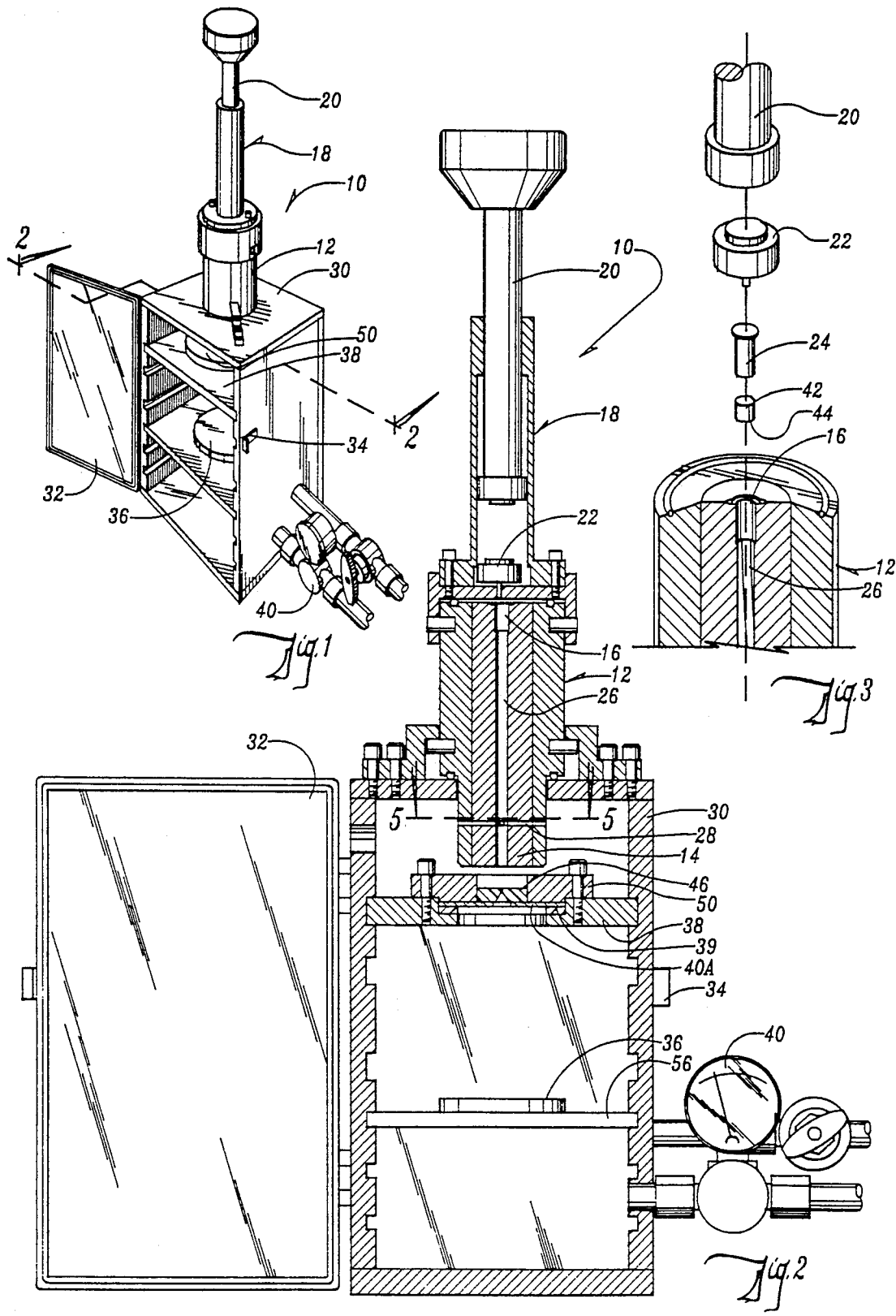

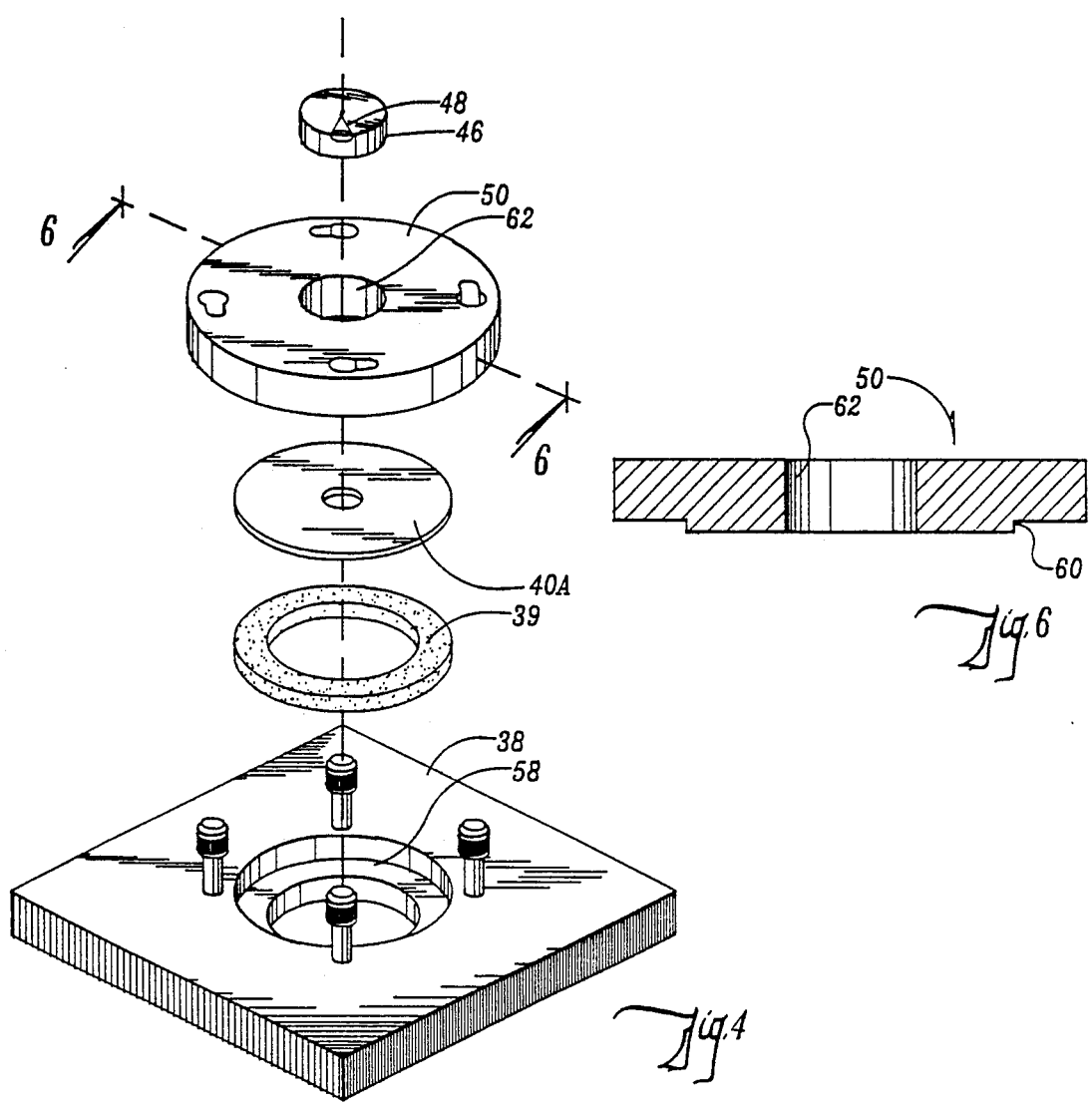
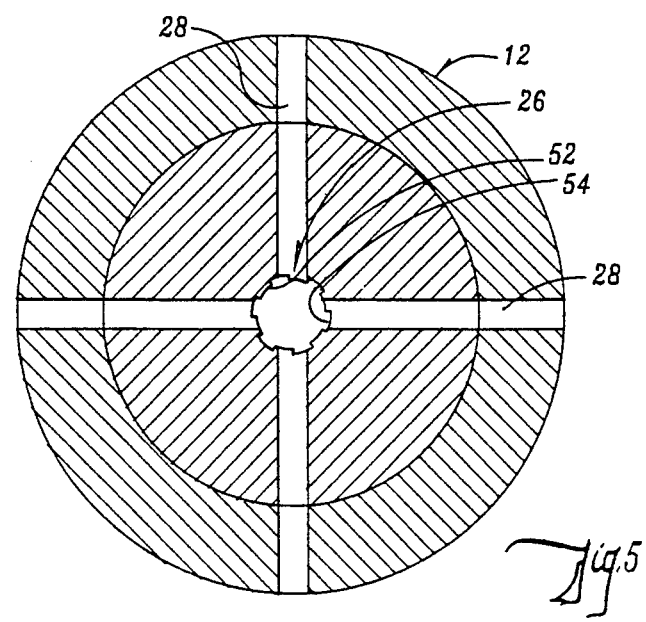

PARTICLE GUN

This is a continuation of copending application Ser. No. 07/351,075 filed on May 12, 1989 now abandoned.

BACKGROUND OF THE INVENTION

This invention relates to an improved particle gun for transferring biological materials such as nucleic acids into the cytoplasm of living cells. With the rapid advancement of recombinant DNA technology, there is a wide-ranging need for biologists to transfer biologic substances from one cell to another, and to transfer synthetic biological material into living cells to exert their activity therein. Such materials can include biological stains, proteins (antibodies or enzymes), and, most commonly, nucleic acids genetic material (either RNA or DNA). Most of the techniques used are painstakingly slow and use methods which transport materials into, at most, only a few cells at a time. More recently, there has been developed a particle bombardment process which utilizes a particle gun, as described in Sanford, et al, 1987, "Delivery of Substances Into Cells And Tissues Using A Particle Bombardment Process," *Journal of Particle Science and Technology* 5:27-37, the disclosures of which are hereby incorporated herein by reference. The basic particle gun disclosed in this article is illustrated at FIG. 3 of page 33 of the article. There it can be seen that the particle gun comprises a firing pin, barrel, a macroprojectile and a stopping plate, surrounded by a vacuum chamber. The barrel of the Sanford et al. gun has a smooth bore. In using a particle gun to transfer biological material into the cytoplasm of living target cells, it is important to avoid carrying unwanted debris into the cells which might result in damage or death to a large number of cells. Debris is undesirable because it may interfere with the success of the procedure; in fact it may cause the target cells to die. Unwanted cellular damage referred to as "blow by" results from debris that occurs when the macroprojectile is too small for the smooth bore barrel, or may result when the macroprojectile or stopping plate materials fail. Failure of the macroprojectile results in small particles of the ultra high molecular weight polyethylene (UHMWPE) material typically used extruding through the stopping plate at a high velocity. Stopping plate failure results when small pieces of the polycarbonate stopping plate are released from the plate upon impact by the macroprojectile. Any one of these sources of debris can substantially lower efficiency and increase unwanted cellular damage or death. The prior art particle gun has a vent near the forward muzzle end of the barrel. However, this venting, even when used with an associated vacuum, is unsuccessful in preventing blow by.

Another problem with the earlier-described Sanford et al. particle gun is poor tolerance for macroprojectile size variations within the range normally obtained by conventional manufacturing methods, whether machining or extrusion. Since the macroprojectiles manufactured from UHMWPE vary in size by as much as 0.002 inches as they are delivered, many of these must be discarded.

Accordingly, one objective of the present invention is to provide an improved particle gun which produces an increased number of transformed cells while at the same time lessening the risk of cell damage or death. Another objective of the present invention is to further increase the number of transformed cells by employing inert high mass metallic beads as microprojectiles in combination with certain preferred polyamine adjuvant materials.

The method and means of accomplishing each of these objectives will become apparent from the detailed description of the invention which follows hereinafter.

BRIEF DESCRIPTION OF THE DRAWINGS

FIG. 1 is a perspective view of the improved particle gun of this invention.

FIG. 2 shows an elevated front view in partial section along line 2—2 of FIG. 1.

FIG. 3 shows an exploded view of the rifled barrel, the firing pin, cartridge and macroprojectile.

FIG. 4 shows an exploded view of the stopping plate and stopping plate holder assembly.

FIG. 5 is a sectional view taken along line 5—5 of FIG. 2 and shows the rifled barrel.

FIG. 6 is a sectional view of the stopping plate holder taken along line 6—6 of FIG. 4.

SUMMARY OF THE INVENTION

This invention relates to a particle gun for transporting biological materials such as DNA and RNA into the cytoplasm or nuclei of living intact target cells. The improvement in the particle gun primarily rests in rifling the bore of the gun barrel, rather than leaving it smooth as in the prior art. The result is a lessening of failures, a lessening of the risk of blow by damage to the target cells, and an improved transformation or material transfer rate. The invention also relates to an improved macroprojectile and to a method of transport of biological materials by an improved bombardment process as well as to a method of preparing microprojectiles for use in the process.

DETAILED DESCRIPTION OF THE INVENTION

FIGS. 1 and 2 illustrate the improved particle gun of this invention. The basic components of the gun, referred to generally at 10, are the barrel 12 having a muzzle end 14 and a chamber end 16. A removable hand firing bolt apparatus is depicted at 18 and generally comprises a downwardly removable ram 20 which strikes on firing pin 22. The entire bolt apparatus 18 may be removed by a simple twist so that a new cartridge 24 may be placed in chamber 16. The firing pin apparatus 22 is of conventional construction for 0.22 cal. rimfire cartridges and will not be further described herein.

The bore 26 of barrel 12 has a vent 28 near its muzzle end 14. An enclosed stainless steel chamber box 30 surrounds muzzle end 14. It has a hinged door 32 which may be unlatched and opened or closed via a latch 34. Inside of enclosure chamber 30 is a petri dish 36, a sample tray 56 and a stopping plate holder shelf 38. Petri dish 36 rests on sample tray 56 in such position that target cells in the petri dish are located on the axis of barrel 26. Sample tray 56 and stopping plate holder shelf 38 are slidably removable from the chamber 30. Chamber 30 is in communication with a vacuum means designated at 40.

The particle gun is loaded for use to transport biological material in the following manner. A macroprojectile 42 is inserted into the chamber 16 and pushed downwardly into the bore 26. The forward end 44 of the macroprojectile carries a small amount of biological material (DNA, for example) mixed with a carrier. The carrier generally comprises a substantially inert metal in the form of small beads which function as microprojectiles. Generally the microprojectiles have diameters within the range of from about 1 micron to about 4 microns. These beads can be made from tungsten, palladium, iridium, platinum or gold. Tungsten is preferred. The most preferred bead diameter is from about 1 micron to about 1.5 microns.

In the most preferred process, the beads are mixed with a small amount of biological material such as DNA or RNA. This is mixed with calcium chloride and a certain amount of polyamine is added.

Generally the ranges of each of these ingredients should be as follows:

Twenty-five ul of tungsten particles at a concentration of 50–200 mg in 2 ml sterile water are placed in a sterile 10 ml centrifuge tube and agitated to suspend the beads. The preferred amount of beads is 100 mg/2 ml. Twenty-five ul of the suspended tungsten beads are placed in an Eppendorf tube and DNA is added at a concentration of 1 ug/ul with the amount varying between 1 ul and 20 ul, the preferred amount being 10 ml. A calcium chloride solution of 25 ul and having a concentration between 1.0–4.0 M, preferably 2.5 M is mixed with the DNA/bead mixture.

While addition of spermidine to the biological material/microprojectile combination has been previously employed, it has now been more broadly discovered that addition of a variety of polyamines to mixtures of tungsten beads and DNA or RNA in preparing microprojectiles significantly improves rates of transformation. While not intending to be limited by theory, it is believed that the polyamine improves delivery of biological material to the cells in this process by improving adherence of the materials to the microprojectile beads. Suitable polyamines have been found to include, for example, spermine, spermidine, caldine, thermine, and the like. The preferred polyamine, spermine, has been found to be superior to the previously disclosed spermidine additive. Accordingly, at this point a polyamine, preferably spermine, in an amount of 10 ul and a concentration between 0.05M and 0.5M, preferably at 0.1M is added followed by finger vortexing. This mixture is allowed to stand for 10 minutes prior to centrifugation for one to two minutes at 9,000 rpm. The microprojectile mixture forms a pellet at the bottom of the Eppendorf tube. Before use, supernatant is withdrawn from the tube to provide a final volume of 30 ul.

The DNA/bead mixture is sonicated briefly to suspend the microprojectiles prior to use. The suspended microprojectiles carrying the biological material are transferred to the forward end of the macroprojectile by micropipette in aliquots of 1–5 ul, with 1.5 ul preferred.

The macroprojectile 42 is placed into the barrel bore 26 forward of chamber 16 or, if the macroprojectile is slightly oversized for the barrel bore, at the bore end of the chamber 16. Chamber 16, being dimensioned for a 22 cal. long rifle cartridge, is able to accept both the macroprojectile and the blank cartridge. The 0.22 cal. blank cartridge 24 is then inserted into chamber 16. The bolt apparatus designated generally at 18 is then placed on top of the barrel and ram 20 thrust downwards such that firing pin 22 hits the rim of the cartridge 24 and fires it. A vacuum is pulled in the vacuum chamber during the firing process, and generally the vacuum provided by vacuum means 40 should be within the range of from about 25 to 29 inches of mercury, i.e. a light vacuum. When the blank cartridge is fired the macroprojectile 42 is propelled out of the barrel at muzzle end 14.

The macroprojectile 42 comes out of muzzle end 14 and almost immediately impacts against stopping plate 46. The microprojectiles, carrying the biological material, pass through orifice 48, forwardly through the frustoconical bore in stopping plate 46, and in shotgun pattern impinge against target cells in petri dish 36. In this manner a host of target cells are simultaneously impregnated with the DNA material.

As best illustrated in FIGS. 4 and 6, the stopping plate holder shelf has a cylindrical recess 58 into which cushion ring 39 and stopping plate support 40A are inserted. Topping these, metal stopping plate holder 50 is affixed to stopping plate holder shelf 38 so that annular projection 60 on the underside of stopping plate holder 50 is concentrically seated in recess 58. Stopping plate 46 is then inserted into opening 62 in stopping plate holder 50. Care is taken that stopping plate holder shelf 38, stopping plate holder 50 and stopping plate 46 are dimensioned and positioned such that orifice 48 is coaxial with barrel 26.

In prior art particle guns, several problems have existed which cause a large incidence of failure. The prior art particle gun is subject to large variation and debris "blow by" and variation of velocity from macroprojectile to macroprojectile due to differences in diameter. Differences in diameter of the macroprojectile as small as 0.0005 inches result in lowered velocity (undersized) or inability to place the macroprojectile in the bore of the barrel (FIG. 3, 26) (oversized). These problems have been solved in the present invention by making chamber 16 of 0.22 cal. long rifle length and by making the bore 26 a rifled bore as shown in FIG. 5 at 52 and 54.

The 0.22 cal. long rifle bore allows many sizes of macroprojectiles between 0.218 inches and 0.222 inches to be easily accommodated in the chamber along with the blank cartridge. When the smooth bore of the prior art particle guns is replaced with the rifle bore of the present gun, preferably having a quarter twist for every six inches, it is found that there is an effective seal presented between the macroprojectile and the bore 26. The result is that macroprojectiles of varying sizes produced by normal manufacturing methods can be employed and remain effectively sealed in the bore, maintaining consistent velocity from firing to firing. Thus the risk of cell damage from "blow by" is substantially reduced. Moreover, the risk of complete failure of undersized macroprojectiles to pass through the barrel (because of extreme blow by) is removed. In addition, the barrel is effectively-cleaned during each firing, so that particulates which precede the macro and microprojectiles are unlikely to occur. This result is surprising because one would ordinarily expect that rifling might cause abrasion to the macroprojectile, resulting in additional debris. Spin imparted to the macroprojectile by the rifling might also be expected to cause loss of the microprojectile and associated biological material from the tip of the macroprojectile; however, this does not occur.

Another important improvement of the present invention is the composition of the macroprojectile. In the prior art, the macroprojectile has been made from somewhat resilient thermoplastic polymeric materials, particularly ultra high molecular weight polyethylene, which has contributed to a high level of failures. In particular, the impact caused by firing of the cartridge has in some instances caused the macroprojectile to deteriorate upon impact with the stopping plate, resulting in extrusion of portions of the macroprojectile through the stopping plate. This produces particulate debris which interferes with the successful introduction of the biological material into the cells by damaging the cells and can actually drive the cells out of petri dish 36 or even damage the dish itself. It has been found, however, that if the prior art UHMWPE material is replaced with a harder material such as acetal, preferably that sold under the trademark POLYPENCO TM, available from Westlakes Plastics Company of Lenni, Pa. 19052, the risk of failures is substantially decreased, yet shattering the macroprojectile or the stopping plate does not occur. In addition, this selection of materials not only reduces the failure rate of the gun, it surprisingly increases the numbers of transformed cells in successful bombardments.

The following examples are offered to further illustrate the apparatus and methods of the present invention, without being limiting thereof.

EXAMPLE I

The performance of the smooth bore and rifled bore barrels was compared using a gene for the enzyme beta glucuronidase (GUS) gene in black Mexican sweet (BMS) maize tissue culture cells. The DNA was constructed such that it was capable of functioning in plant cells and could be detected by a well known cytochemical staining procedure. The DNA was mixed with beads as indicated previously. BMS suspension cells of maize were prepared for the particle gun by subdividing the suspension culture cells into 100 mg aliquots on filter paper in 3.3 cm petri plates. Each treatment unit consisted of a petri dish with 100 mg of maize cells. Following particle gun bombardment, cells were incubated for 48 hours and stained by addition of 5-Bromo-4-Chloro-3-Indolyl-Beta-D Glucuronide (X-Glu) The results of this experiment are shown in Table 1. The smooth bore barrel had a 30% failure rate, i.e. failure to produce transient expression of the beta glucuronidase gene in the bombarded cells. Twenty percent of the samples had velocity which was so low that there were no stained cells, while an additional 10% showed sample damage in which some cells were blown off the filter paper and a hole was observed in the filter paper as well. The rifled bore barrel had a zero failure rate. In addition, in comparing only those samples in which transient expression of the beta glucuronidase gene was observed, the rifle bore barrel produced approximately 15% more stained cells per plate than the smooth bore barrel.

TABLE 1

Comparison of Smooth Bore and Rifled Barrel Failure Rate and Transient Gene Expression Using a Cytochemical Stain for Expression of the Beta Glucuronidase Gene (GUS) in Black Mexican Suspension Cells of Maize

| Barrel Type | Porportion of Failure | | Number Samples | Mean Number Expressing Cells |
|---|---|---|---|---|
| | Low Velocity | Sample Damage | | |
| Smooth | 20% | 10% | 10 | 130.6 |
| Rifled | 0% | 0% | 10 | 148.7 |

EXAMPLE II

Two macroprojectile materials, ultra high molecular weight polyethylene and acetal, were compared using the GUS gene in transient expression experiments using maize suspension culture cells and tobacco suspension culture cells. The number of stained cells was measured as in the previous experiments. Results are shown in Table 2. Summarized over the six separate experiments, the acetal macroprojectile produces 70% more stained cells than the ultra high molecular weight polyethylone macroprojectile.

TABLE 2

Transient Gene Expression of Ultra High Molecular Weight Polyethelene and Acetal Microprojectiles Using the GUS Gene over Several Experiments

| Experiment Number | Species | UHMW-P | | Acetal | |
|---|---|---|---|---|---|
| | | N | Total Stained Cells | N | Total Stained Cells |
| 1 | Maize | 4 | 186 | 5 | 338 |
| 2 | Maize | 9 | 315 | 10 | 485 |
| 3 | Maize | 5 | 52 | 5 | 65 |
| 4 | Maize | 6 | 50 | 4 | 64 |
| 5 | Tobacco | 5 | 122 | 2 | 143 |
| 6 | Tobacco | 5 | 64 | 8 | 221 |
| Summary | | 34 | 789 | 34 | 1317 |
| Mean | | | 131.5 | | 219.5 |

EXAMPLE III

The method of combining tungsten beads and DNA was altered in another series of experiments using two polyamines, spermidine and spermine. As shown in Table 3, the use of spermine produced 2.5 times more transformed cells than spermidine.

TABLE 3

Comparison of Transient GUS Gene Expression Between Spermidine and Spermine Polyamines in DNA/Bead Mixtures in Tobacco and Maize Suspension Cultures

| Species | N | Mean Number Stained Cells | |
|---|---|---|---|
| | | Spermidine | Spermine |
| Tobacco | 28 | 20.6 | 69.9 |
| Maize | 20 | 42.4 | 113.2 |

What is claimed is:

1. A particle biological material transport gun for transporting biological material into living cells, said particle gun comprising:
   means for holding living cells;
   a barrel comprising,
      a bore along its length,
      a muzzle defined at one end of the bore wherein said muzzle is aimed at said means for holding living cells,
      a cartridge chamber defined at the other end of the bore and constructed so as to hold a firing cartridge,
      an acetal plastic macroprojectile for carrying biological material, wherein said macroprojectile is constructed with a diameter and arranged such that said macroprojectile travels within said bore from said cartridge chamber to said muzzle when the cartridge is fired, and
      wherein said bore is rifled such that consistent velocities are produced regardless of variations in the diameter of said macroprojectile;
   firing pin means operatively associated with the cartridge chamber for firing the cartridge;
   a stopping plate positioned between said muzzle and said means and holding living cells for stopping said macroprojectile, the stopping plate having an orifice which allows the biological material carried on the macroprojectile to pass therethrough; and a vacuum chamber surrounding said muzzle, said stopping plate, and said means for holding living cells.

2. The particle gun of claim 1 wherein the rifled bore has a twist over the barrel length.

3. The particle gun of claim 2 wherein the barrel has a vent proximal to said muzzle for gas and debris release.

4. The particle gun according to claim 2 wherein said twist is one quarter twist every six inches.

5. The particle gun according to claim 1 wherein said cartridge chamber is longer than the length of the cartridge used in firing.

6. The particle gun according to claim 5 wherein said barrel is constructed to be used with 0.22 caliber long rifle cartridge.

7. The particle gun according to claim 1 wherein said barrel is constructed to be used with 0.22 caliber long rifle cartridge and said diameter of said macroprojectile is between 0.218 inches and 0.222 inches.

* * * * *